United States Patent [19]

Burnham et al.

[11] Patent Number: 4,531,058

[45] Date of Patent: Jul. 23, 1985

[54] POSITRON SOURCE POSITION SENSING DETECTOR AND ELECTRONICS

[75] Inventors: Charles A. Burnham, South Essex; John F. Bradshaw, Jr., Winthrop; David E. Kaufman, Brockton; David A. Chesler, Newton Highlands; Gordon L. Brownell, Cambridge, all of Mass.

[73] Assignee: The Massachusetts General Hospital, Boston, Mass.

[21] Appl. No.: 343,558

[22] Filed: Jan. 28, 1982

[51] Int. Cl.³ ............................................. G01T 1/20
[52] U.S. Cl. ................................ 250/363 S; 250/366
[58] Field of Search ............... 250/363 R, 363 S, 366, 250/369

[56] References Cited

U.S. PATENT DOCUMENTS

| | | | |
|---|---|---|---|
| 3,432,660 | 3/1969 | Anger | 250/363 S |
| 3,732,419 | 5/1973 | Kulberg et al. | 250/363 S |
| 3,851,177 | 11/1974 | Van Dijk et al. | 250/366 |
| 3,859,531 | 1/1975 | Van Dijk | 250/366 |
| 3,862,425 | 1/1975 | Myers | 250/366 |
| 3,908,128 | 9/1975 | Richey | 250/366 |
| 3,937,964 | 2/1976 | Muehllehner | 250/366 |
| 3,970,852 | 7/1976 | Richey et al. | 250/363 S |
| 4,071,762 | 1/1978 | Lange et al. | 250/369 |
| 4,142,102 | 2/1979 | Lange | 250/369 |
| 4,197,583 | 4/1980 | Westell et al. | 250/363 S |
| 4,223,221 | 9/1980 | Gambini et al. | 250/363 S |
| 4,250,385 | 2/1981 | Luderer et al. | 250/363 S |
| 4,262,207 | 4/1981 | Tosswill | 250/363 S |
| 4,274,002 | 6/1981 | Tomita | 250/366 |

OTHER PUBLICATIONS

Tanaka et al., "Scintillation Cameras Based on New Position Arithmetics", *Jour. of Nuc. Med.*, vol. 11, No. 9, pp. 542–547.

Burnham et al., "Application of a One-Dimensional Scintillation Camera in a Positron Tomographic Ring Detector".

Burnham et al., "One Dimensional Scintillation Cameras for Positron ECT Ring Detectors" *IEEE Trans. on Nuc. Sci.*, vol. NS-28, No. 1, Feb. 1981, pp.109–113.

*Primary Examiner*—Janice A. Howell
*Attorney, Agent, or Firm*—Weingarten, Schurgin Gagnebin & Hayes

[57] ABSTRACT

A positron source, position sensing device, particularly with medical applications, in which positron induced gamma radiation is detected using a ring of stacked, individual scintillation crystals, a plurality of photodetectors, separated from the scintillation crystals by a light guide, and high resolution position interpolation electronics. Preferably the scintillation crystals are several times more numerous than the photodetectors with each crystal being responsible for a single scintillation event from a received gamma ray. The light guide will disperse the light emitted from gamma ray absorption over several photodetectors. Processing electronics for the output of the photodetectors resolves the location of the scintillation event to a fraction of the dimension of each photodetector. Because each positron absorption results in two 180° oppositely traveling gamma rays, the detection of scintillation in pairs permits location of the positron source in a manner useful for diagnostic purposes. The processing electronics simultaneously responds to the outputs of the photodetectors to locate the scintillations to the source crystal. While it is preferable that the scintillation crystal include a plurality of stacked crystal elements, the resolving power of the processing electronics is also applicable to continuous crystal scintillators.

23 Claims, 11 Drawing Figures

POSITRON SOURCE POSITION SENSING DETECTOR AND ELECTRONICS

This work was supported in part by the United States Government under contract with the Department of Energy and the National Institute of Health.

FIELD AND BACKGROUND OF THE INVENTION

In the present invention, the position of a positron source, typically within the body for purposes of medical diagnosis, is determined by detection of the pair of oppositely traveling gamma rays produced by electron collision with the emitted positrons after only a short trajectory. By simultaneously detecting the location of the two gamma rays, positional information on the positron source is obtainable.

Typically, detection of the gamma rays is accomplished using a gamma radiation scintillating crystal such as sodium iodide crystal with the resulting photo emission detected by a photomultiplier tube. In some systems each photomultiplier has a single crystal associated with it, leaving gaps between the crystals. In order to improve the resolution of the system, the entire ensemble of crystals and photomultiplier tubes is moved in a time dependent fashion. Where the activity under investigation is a time varying phenomena, this time dependent detection will produce a blurring and result in a loss of diagnostic information.

An example of another system is shown in Tanaka, "Scintillation Cameras Based On New Position Arithmetic", Journal of Nuclear Medicine, Volume 11, No.9. A single large crystal spans several photomultipliers and uses a delay line to transpose position and time to locate a scintillation point. This system, however, is limited in the rate at which events can be processed.

Another problem from the use of a large single crystal is due to the uncertainty of the actual depth within the crystal at which scintillation occurs. The depth of scintillation affects the dispersion of the light ultimately received by the photodetectors. This in turn varies the output of the photodetectors independently of gamma ray trajectory. Additionally, when a scintillation occurs near an edge of the crystal, edge effects will alter the light dispersion pattern received by the photodetectors and thus tend to distort the sensing of the position of the scintillation point.

BRIEF SUMMARY OF THE INVENTION

In accordance with the teaching of the present invention, a positron camera, using photo detection of gamma radiation scintillation, is provided in which the scintillation elements are comprised of a large number of stacked scintillation crystals, the light output of which is dispersed across several photodetectors whose light output is in turn analyzed by a real time spatial filter that resolves scintillation location down to a single crystal element despite the fact that each photodetector receives light from several scintillation crystals.

The scintillation crystals are typically formed in a ring about the subject under investigation and comprise a plurality of thin, typically half centimeter thick crystals, each within its own housing and stacked side-by-side. A plexiglass light guide disperses the light between the individual scintillation crystals and a plurality of photomultiplier tubes arrayed in a single line around the periphery of the ring. Typically several such rings are axially stacked together to provide positron emission sensing over a larger solid angle. Regardless of where scintillation occurs within each scintillation crystal, that light will be conducted to the surface of the scintillating crystal facing on the light guide and dispersed via the light guide to the photomultipliers.

The output of each photomultiplier is applied to an array of amplifiers, typically one amplifier corresponding to each scintillation crystal. There are typically four or five times as many scintillation crystals, and amplifiers, as there are photomultiplier tubes. The output of each photomultiplier tube is applied to several amplifiers each with a different weighting, which may include signal inversion, in accordance with a weighting formula. The weighting formula is based upon initial calibration to normalize the outputs of the scintillation crystals as well as photomultiplier tubes and provides processing which resolves scintillation location to an individual scintillation crystal. This location is determined to a dimension that is a small fraction of the actual light aperture of an individual photomultiplier tube. The outputs of the amplifiers are used to detect a transition from a signal level of one polarity to a signal level of another polarity, in a predetermined direction, indicative of the position of the scintillation. To distinguish a true scintillation event from background scintillations, a discriminator circuit is utilized to generate a coarse position signal based on time, position and energy levels. The coarse position defines a position range for acceptable scintillation position sensing. Detection of a polarity transition within this position range sets a bit in an output register which is then available to external processing electronics as an indication of the location of the scintillation event. Further processing for positron source information, by known techniques, can then be utilized from this positional information.

While it is preferred that the scintillation detector comprise a plurality of individual thin crystals, the present invention will also provide real time optimal spatial resolution for detection of a scintillation point in a single, or several large scintillation crystals.

DESCRIPTION OF THE DRAWING

These and other features of the present invention are more fully set forth below in the solely exemplary detailed description and accompanying drawing of which.

DETAILED DESCRIPTION

The present invention contemplates a positron camera in which the oppositely traveling gamma radiation emitted from positron electron collision is detected by scintillation in a scintillation crystal, preferably formed as a plurality of thin, stacked scintillation crystals. Light is sensed, as a result of each scintillation event, in photomultiplier tubes and is real time, spatially filtered to provide a resolution for the location of the scintillation event which is a fraction of the light receiving aperture of each photomultiplier tube.

Figure 1:
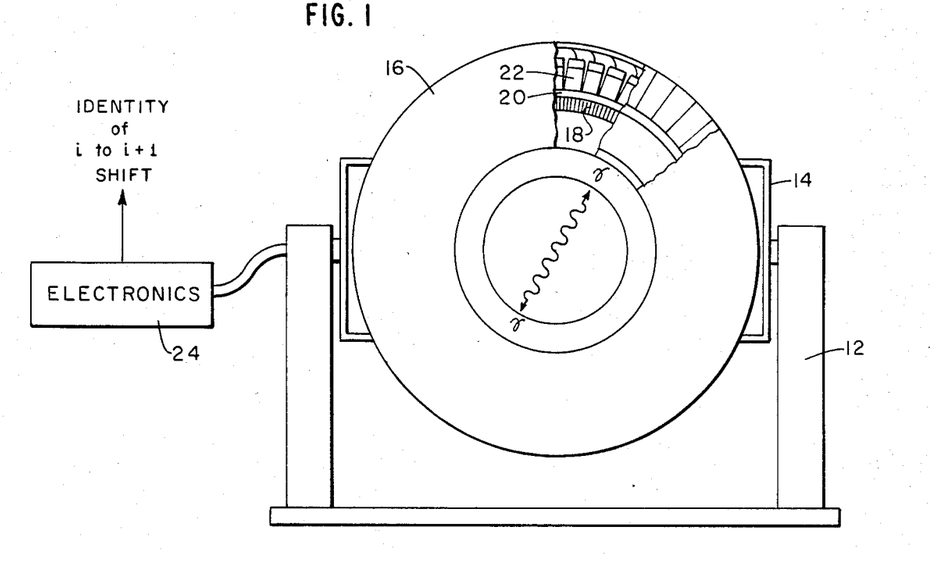
FIG. 1 is a side pictorial view of a positron camera, partially cutaway, in accordance with the present invention.

Such a positron camera is illustrated in FIG. 1 in which a movable stand 12 supports on gimbals 14 a ring 16 of a positron camera comprising an annular row 18 of stacked scintillation detectors having crystals, such as sodium iodide or bismuth germanate (BGO). Radially outward from the stacked row 18 is a light guide 20, typically formed of plexiglass, and separating the row 18 from an array 22 of photomultiplier tubes. The photomultiplier tubes are positioned to receive light emitted by scintillation events within the row 18 of detectors. Electronics 24 are provided to not only power the photomultipliers in the array 22 but to process their output signals in a manner to indicate the location of each scintillation event in terms of each single detector crystal in the row 18.

Figure 2:
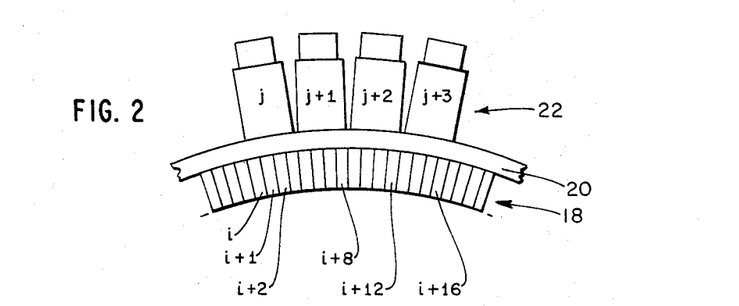
FIG. 2 is a more detailed view of the scintillation detector and photo detector portions of the positron camera of FIG. 1.

With reference to FIG. 2, an expanded view is shown of the row 18 of scintillation detectors, the annular light guide 20 and the array 22 of photo detectors. Each scintillation detector in the row 18 is identified in a numerically ascending order by the designation i, while each photomultiplier in the array 22 is designated, in ascending order likewise, by the designation j. Each photomultiplier tube j in the array 22 will be of a dimension which corresponds to the thickness in the direction of the row 18 of four scintillation crystal detectors i.

Figure 3:
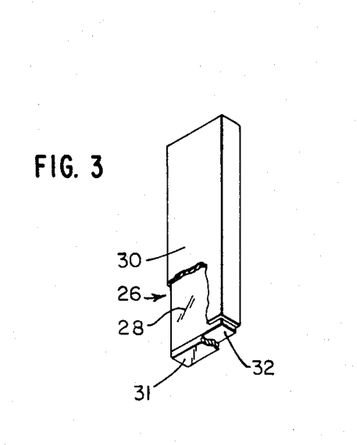
FIG. 3 is a partially broken away perspective view of a single scintillation detector element according to the present invention.

FIG. 3 illustrates such a detector element i as comprising a rectangular block of scintillation crystal 26, which may be a sodium iodide or bismuth germanate (BGO) crystal, as indicated above and surrounded by a light reflective coating 28. In the case of sodium iodide, the crystal 26 is encased in an aluminum outer frame 30 and is faced with a cover glass 31 to avoid water absorption. An outer surface 32 of the crystal 26 faces the light guide 20 through cover glass 31 in such manner as to transmit light from the crystal 26 directly into the light guide 20. Regardless of the location of scintillation within the crystal 26, internal reflections will direct nearly all of the light from each scintillation event to the surface 32 in a manner to provide the identical dispersion through the light guide 20 to the photomultipliers j. This makes the camera substantially independent of depth of penetration of the gamma ray into the crystal 26 before scintillation occurs. Preferrably no gamma ray absorber is used between crystals. Even where a gamma ray produces scintillations in more than one crystal, the photomultipliers will process it as a single event.

Typical crystals may be of a thickness of one-half centimeter in the direction in which they are stacked within row 18 and may be up to two centimeters in the opposite width and five or six centimeters in length. The total thickness of the element i, including the reflector 28 and aluminum layer 30, will be such as to typically stack four such elements, in the stacking direction, across the faces 34 of each photomultiplier tube j.

Figure 4A:
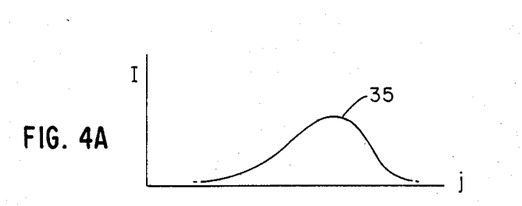
FIGS. 4A and 4B are waveform diagrams useful in illustrating light disbursal according to the present invention and the prior art respectively.
Figure 4B:
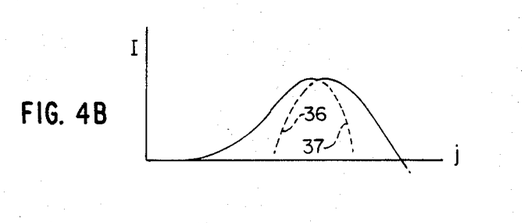

The light guide 20, typically fabricated of plexiglass and approximately two centimeters in thickness in the radial direction (or typically one half of the diameter of the photomultiplier tube) provides a spreading of the light emanating from the end face 32 and coverglass 31 of each scintillation crystal 26. Such a distribution is typically illustrated by the waveform 35 in FIG. 4A. Here the vertical axis represents intensity while the horizontal axis, expressed in j numbers, represents distance in terms of photomultiplier dimensions. The use of a plurality of thin scintillation elements i comprising individual slices of scintillation crystals 26 produces a homogeneous bell shaped character to the distribution curve 35 regardless of the point at which scintillation takes place. In the case where a single crystal or a small number of large crystals is utilized in lieu of the many thin ones in the row 18 the presence of a scintillation near a crystal edge is likely to produce a distribution illustrated in FIG. 4B having truncated tails 36 or 37 depending upon the location of the point of scintillation with respect to a crystal edge. Such a variation in distribution will produce an error in the detected position information for those scintillations occuring near crystal edges. The vast number of stacked elements illustrated in FIG. 2 in the ring 18 avoids this uncertainty.

Figure 5:
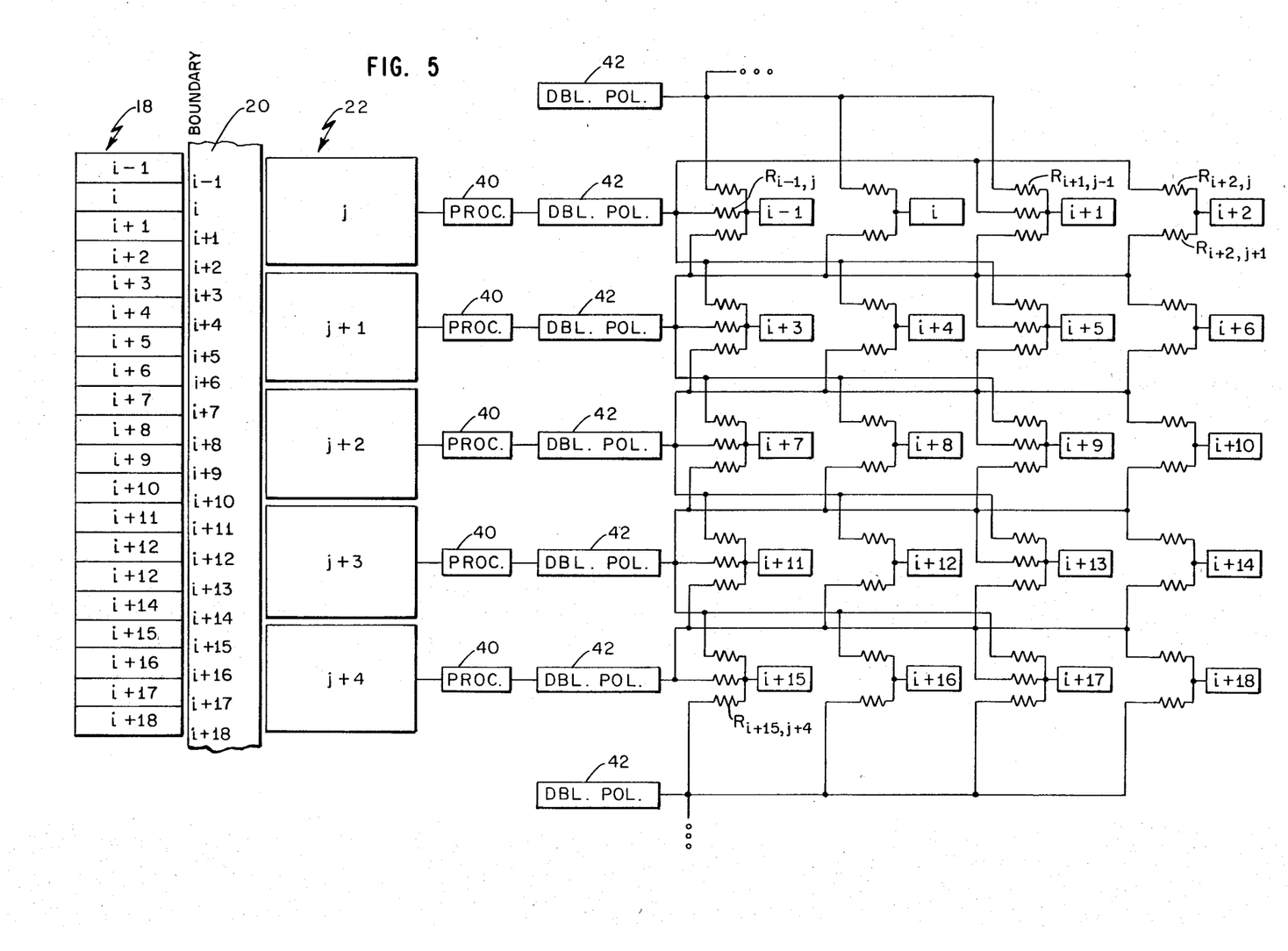
FIG. 5 is a detailed circuit diagram of the processing electronics for the output of the photomultiplier tubes of FIG. 2.

In FIG. 5, the circuitry associated with a portion of the row 18, light guide 20, and array 22 of photomultipliers is illustrated. Each photomultiplier j in the array 22 has its output applied through a processor or filtration circuit 40, as known in the art, to provide signal shortening and integration, and to limit the output signal period to permit more accurate and frequent scintillation events to be monitored. The output of each filtration circuit 40 is applied to a double polarity converter 42, the function of which is to provide outputs of positive and negative polarity at the same magnitude as the magnitude of the input signal. This is provided so that, as will be illustrated below, where further signal processing requires that the output of each photomultiplier be not only scaled in magnitude but altered in polarity, a signal of the opposite polarity will be available for that purpose. The output of each of the polarity converter circuits 42, either positive or negative as necessary, is applied through weighting resistors $R_{i,j}$ to a set of amplifiers $i-1, i, i+1 \ldots i+n$. Each of the amplifiers corresponds to a boundary between two scintillation elements, the amplifier i corresponding to the boundary between scintillation elements i and $i+1$. Each of the amplifiers $i \ldots i+n$ receives inputs from three converters 42 and corresponding photomultipliers j through respective resistors $R_{i,j}$. In effect, each photomultiplier provides its output to a total of twelve of the amplifiers $i \ldots i+n$. The amplifiers are shown in FIG. 5 arrayed in rows corresponding to each of the photomultipliers j, with four columns corresponding to each of the scintillator elements i. The output of each photomultiplier will be applied to all four amplifiers in its row, as well as all four amplifiers in the preceding and following rows through suitable resistors $R_{i,j}$. Due to symmetries the amplifiers designated $i+2$, $i+6$, $i+10$, etc., and i, $i+4$, $i+8$, etc., only receive two inputs.

The various values of the resistors $R_{i,j}$ are determined in accordance with a weighting function: $W_{i,j} = (L_{i+1,j-}$ $-L_{i,j})/(L_{i+1,j}+L_{i,j})-B_i$, where $B_i=\Sigma(L_{i+1,j}-L_{i,j})/(L_{i+1,j}+L_{i,j})$. The $L_{i,j}$ values are calibration figures which represent the output of each photomultiplier tube for a reference energy, gamma ray input to each of the i scintillation elements. The summation over j is for all j values, that is photomultipliers, which have an output to a particular amplifier i. The i's designate both the scintillation crystal and associated amplifier concerned. The weighting factors $W_{i,j}$ thus specifically identify the attenuation to be provided by each of the resistors $R_{i,j}$ of the photomultiplier signal applied to its input. In the case where the weighting factor is a negative number, the opposite polarity, from the converter 42 is utilized.

Figures 6, 7, 10:
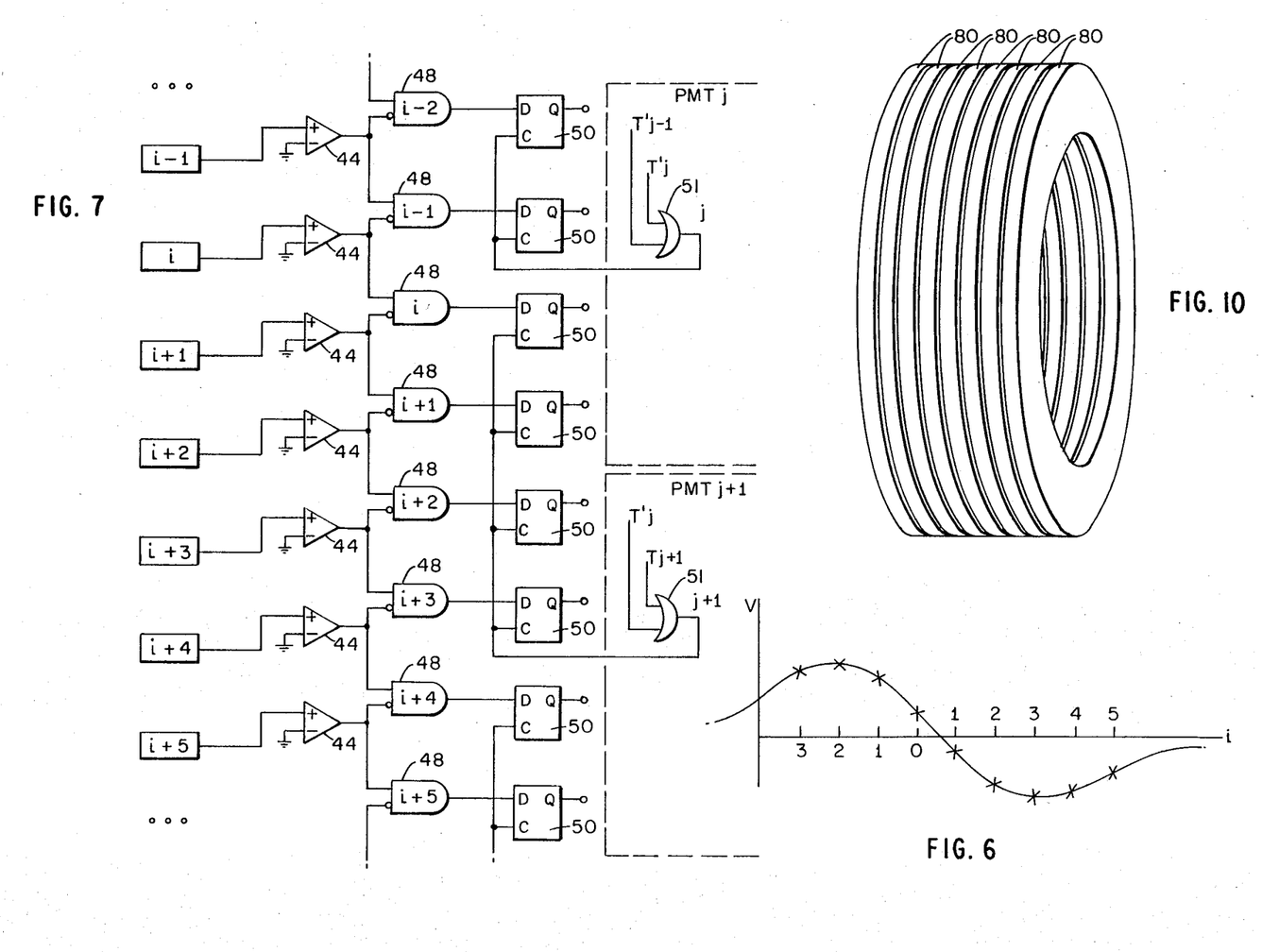
FIG. 6 is a wave form diagram illustrating the response of the electronics of FIG. 5 to a scintillation event.
FIG. 7 is a circuit diagram indicating the final processing circuitry for the signals developed in FIG. 5.
FIG. 10 represents a stacked array of positron camera rings illustrated in FIG. 1 to form a complete positron camera.

FIG. 6 represents the output of amplifiers i over the range $i=-4$ to $i=+5$ for a typical scintillation event in element $i=+1$ (between amplifier $i=0$ and $i=+1$) utilizing the processing circuitry of FIG. 5. As will be seen, the outputs will represent an "S" curve which produces an intensity transition, in the example illustrated, between amplifier $i=0$ and amplifier $i=+1$, corresponding to the scintillation event occurring in the scintillation element $i=+1$.

Further processing electronics illustrated in FIG. 7 is utilized to provide detection of this point. As shown there, the output of each of the amplifiers $i-1, i \ldots i+5 \ldots i+n$ is applied to a noninverting input of respective ones of amplifiers 44. A set of AND gates 48 are provided and labeled with the designations $i-1, i \ldots i+4, \ldots i+n$. From the outputs of amplifiers 44, each gate 48 receives the output of the amplifier of its same name on a noninverting input and the output the next higher amplifier on an inverting input. The gate 48 designated i will thus indicate high inputs from both of its sources when and only when the corresponding amplifiers respectively represent a reversal in polarity from one amplifier to the other, proceeding from a positive to a negative polarity, and thus representing the situation illustrated in FIG. 6 between the $i=0$ and $i=+1$ amplifiers. The output of each of the gates 48 is applied to a respective single bit register 50 which operates to record that value for further processing circuitry to acquire the information.

Each of the registers 50 are clocked in groups of four by OR gates 51 designated $j, j+1 \ldots$ each of which receive two respective input timing signals designated $T'j-1$ and $T'j$ for OR gate 51 designated j, and $T'j$ and $T'j+1$ for OR gate 51 designated $j+1$, and so on in successive order. The gates 51 in conjunction with the timing signals T' define a position range covering a total of eight of the registers 50 which have been selected on the basis of a coarse position determination provided from the circuitry of FIGS. 8 and 9. The coarse positioning signals localize the scintillation, typically to a pair of photomultiplier tubes located with the positron source between them. The coarse positioning circuitry also provides discrimination based upon energy thresholds and time coincidence.

Figure 8:
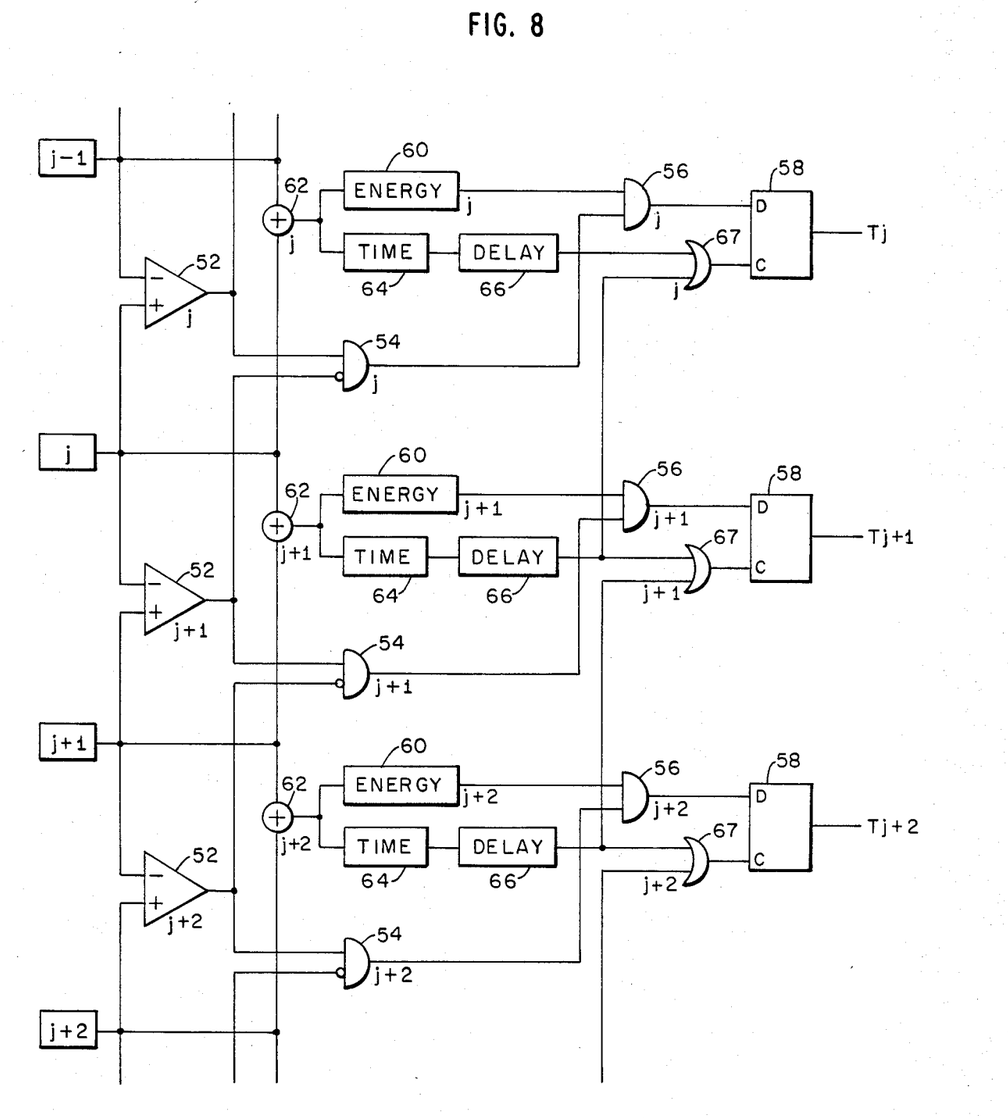
FIGS. 8 and 9 are diagrams of circuitry which provides a coarse position range for scintillation event detection.

Circuitry for accomplishing this function is illustrated in FIG. 8. As shown there, the photomultiplier tubes (PMT) designated $j-1$ through $j+2$ for exemplary purpose provide their output to corresponding position comparitor 52 labeled $j, j+1 \ldots$ in correspondence to the photomultipliers. Each position comparator 52 receives the output of the corresponding photomultiplier on an inverting input and the output of the next higher photomultiplier on a noninverting input. The output of each comparator 52 is applied to a noninverting input of corresponding AND gates 54 designated $j, j+1 \ldots$.

The output of each AND gate 54 is applied to a corresponding noninverting input of a further AND gate 56. The output of each AND gate 56 is applied to the set input of a single-bit, one-shot register 58 designated in j numbers for each corresponding photomultiplier tube. Register 58 typically has a 10 nsec. "on" time.

The AND gates 54 receive on an inverting input, the output from the position sensing comparator 52 next above in the ascending j order. The AND gate 56 receives on a second, noninverting input, the output from an energy threshold circuit 60 corresponding to each of the j photomultiplier tubes. The energy threshold circuit 60 effectively discriminates against sensed levels less than a certain gamma ray energy, typically 120 KV in the case of the sodium iodide detector. The energy discriminator 60 receives from a summing circuit 62 the summation of the output of the corresponding photomultiplier tube in combination with the output of the next higher photomultiplier tube in the j series. The same signal applied to the energy detector 60, typically exhibiting an asymptotic rise over time, is applied to a time of appearance detector circuit 64, one corresponding to each of the photomultiplier tubes in the j series. These circuits 64 operate to detect the time of occurrence of a constant fraction of the combined waveform from the photomultiplier tubes in order to detect the same relative point on the waveform regardless of amplitude. The outputs of the time of occurrence detectors 64 are applied to corresponding delay circuits 66, of approximately a 25 nsec. delay, in order to let the energy and position discriminator circuits 60 and 52 react to the full amplitude values of the photomultiplier tube outputs. The outputs of the delay circuits 66 are applied to clock the corresponding single-bit registers 58 through OR gates 67. Each OR gate 67 receives the output of the corresponding and next higher delay circuit 66. Each of the registers 58 provides an output timing signal designated $Tj, Tj+1 \ldots$.

Figure 9:
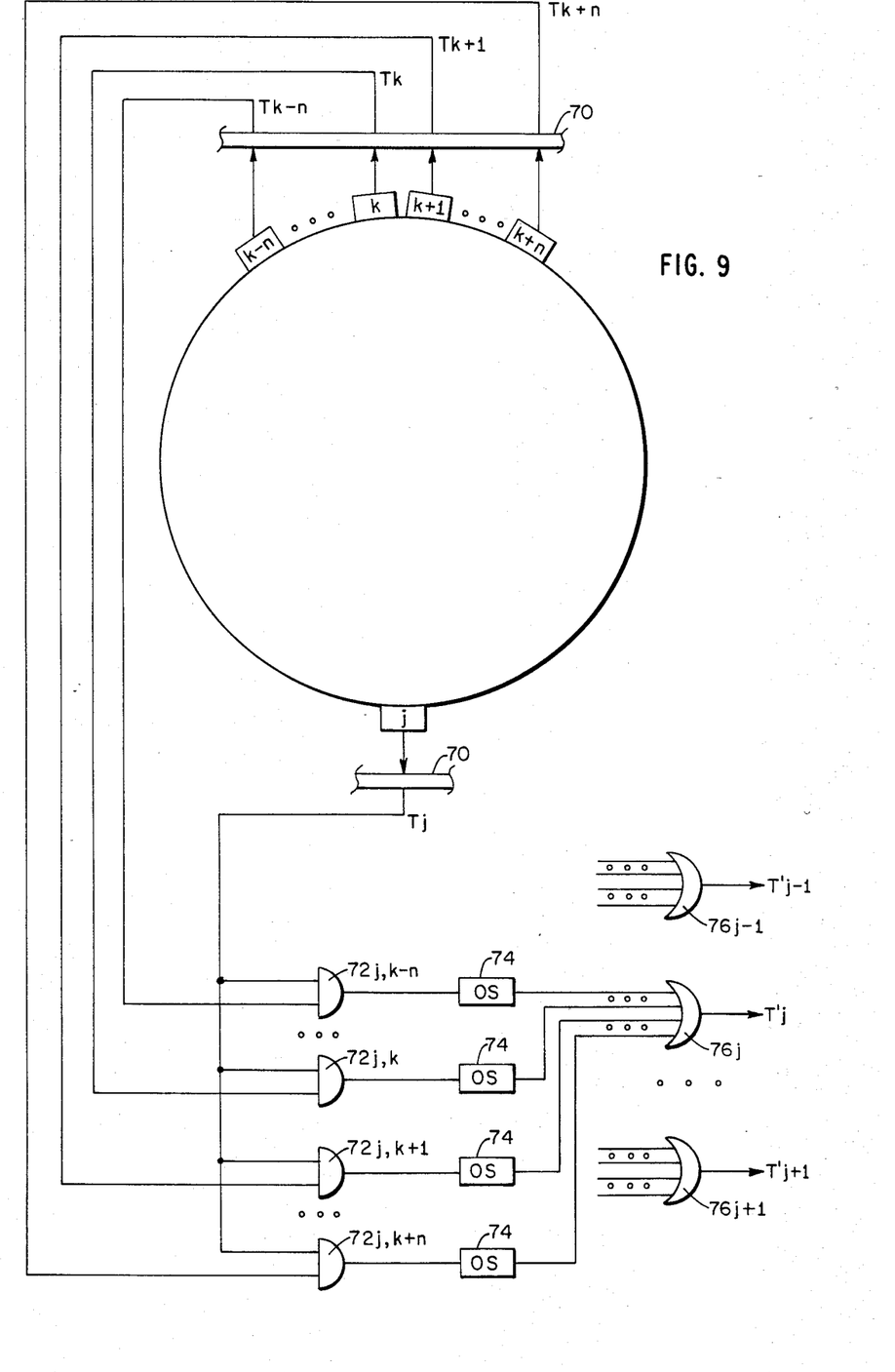

With respect to FIG. 9, an array of the j photo detectors is illustrated in the typical ring configuration in which they are utilized in FIG. 1. The photomultiplier j is shown opposite a range of photomultipliers $k-n \ldots k, k+1 \ldots k+n$ (with n varying over typically one-third of the total photomultipliers). The outputs of the photomultipliers are applied through processing circuitry labeled 70 which corresponds to the circuitry of FIG. 8 and from which the $Tj, Tk-n, Tk, Tk+1 \ldots Tk+n$ signals are provided. The Tj signal is applied to one input of a set of AND gates 72, one corresponding to each of the Tk signals from the range of photomultipliers on the opposite side of the ring. The AND gates 72 receive corresponding inputs from the Tk signals. The output of each of the AND gates 72 is applied to a corresponding single shot registers 74 with the output of all of the single shot register 74 applied to a single OR gate 76. An OR gate 76 is provided for each of the j photomultiplier tubes and provides as a corresponding output the T'j signals utilized in FIG. 7.

In function, the circuitry of FIG. 8 provides position, time, and energy discrimination to arrive at the Tj signals utilized in FIG. 9 and further to provide a Tj signal of short duration to avoid chance coincident events. Position discrimination is provided by the comparitors 52 and AND gates 54. The output of the AND gate 54 will accordingly be set if the output of the photomultiplier tube to which it corresponds is higher than the output of the adjacent photomultipliers tubes, indicating a possible positioning of the scintillation adjacent to that photomultiplier tube. This designation, if present, along with an output from the corresponding energy discriminator 60 indicating a sufficiently high energy level results in AND gate 56 for that corresponding photomultiplier providing a set input to the corresponding single bit register 58. This set input is clocked into the register through the delay line 66 if the timing of the signal is appropriate.

FIG. 9 utilizes the raw information provided in FIG. 8, to compare each Tj signal with a corresponding signal from photomultipliers covering a range on the opposite side of the ring to account for the fact that the position of the positron source will not necessarily be centered within the ring. The AND circuits 72 require that at least one tube in the range of opposite photomultipliers provide an output signal coincident with the j photomultiplier tube in which case a corresponding one of the single shot registers 74 is activated. Activation of any one of the registers 74 will produce an output through the corresponding OR gate 76, producing the T'j signals utilized in FIG. 7 to define a coarse position range which includes the photomultiplier designated j.

As shown in FIG. 10, a complete positron camera will typically utilize a set of axially stacked rings 80 of a predetermined axial length through which a body under study is inserted. Each of the rings 80 corresponds to one of the assemblies illustrated in FIG. 1. In the case where it is desired only to have a positron camera through which the head of a patient is to be inserted, a foot and one-half inside diameter is satisfactory while if an entire torso is to be inserted through the camera, a typical inside diameter of 3 feet is more appropriate.

Thus described above is a positron camera capable of providing information on positron emitting source position with higher resolution and reliability. It should be noted that the above description is solely exemplary, the actual scope of the invention being solely as defined in the following claims.

What is claimed is:

1. A system for sensing the position of a scintillation event comprising:
   scintillation means responsive to radiation received over a field of view to produce a light-emitting interaction therewith;
   said scintillation means being characterized as a plurality of stacked scintillation elements;
   a plurality of photodetectors placed to receive light from said plural stacked elements;
   said photodetectors being less numerous than said scintillation elements and being positioned adjacent each other in a single line such that each of said plural photodetectors will respond to light from a plurality of said stacked elements; and
   means responsive to said plural photodetectors for localizing the light source to one among said plural stacked elements.

2. The system of claim 1 wherein said scintillation elements are internally reflective.

3. The system of claim 1 wherein said plural stacked elements include scintillation crystals.

4. The system of claim 3 wherein said scintillation crystals include sodium iodide.

5. The system of claim 3 wherein said scintillation crystals include BGO.

6. The system of claims 1, 3, 4 or 5 wherein said stacked elements are generally thin in the direction of stacking, transverse to the direction over which radiation is received and generally long in the direction over which radiation is received.

7. The system of claim 1 wherein said photodetectors include photomultiplier tubes.

8. The system of claims 1 or 7 wherein there are at least four stacked elements provided for each one photodetector.

9. The system of claim 1 further including:
   a light guide positioned between said plural stacked elements and said photodetectors and operative to convey and distribute light emissions from said plural stacked elements to plural of said photodetectors.

10. The system of claim 9 wherein said plural stacked elements are internally reflective whereby the light emitted to said light guide is generally insensitive to the depth of scintillation within said stacked elements produced by the received radiation.

11. The system of claim 1 wherein said localizing means includes a real time signal processor.

12. The system of claim 11 wherein said localizing means includes means for identifying the most likely photo-emitting one of said plural stacked elements for each scintillation event.

13. The system of claim 11 wherein said localizing means further includes means for identifying the border of a predetermined side of the most likely to be photo-emitting of the plural stacked elements for each scintillation event.

14. The system of claim 11 wherein said localizing means further includes:
   a plurality of amplifiers;
   each of said plural amplifiers receiving a weighted input from a plurality of said photodetectors;
   each amplifier corresponding to one of said stacked elements; and
   means for identifying where two amplifiers corresponding to adjacent ones of said stacked elements possess opposite signal polarities in a predetermined direction.

15. The system of claim 14 wherein there are four stacked elements corresponding to each photodetector whereby each photodetector is positioned adjacent to two outer and two inner of said plural stacked elements;
   the output of each photodetector being applied to a plurality of said amplifiers with input weightings according to the formulation: $W_{i,j}=(L_{i+1,j}-L_{i,j})/(L_{i+1,j}+L_{i,j})-B_i$, where $B_i=\sum_j(L_{i+1,j}-L_{i,j})/(L_{i+1,j}+L_{i,j})$ where i identifies the individual stacked elements and corresponding amplifiers and j identifies the photodetectors and where $L_{i,j}$ represents the output of the photodetector j when the ith crystal scintillates from a standard source.

16. The system of claim 1 wherein said plural stacked elements of said scintillation means are formed in a ring about an axis.

17. A system for sensing the position of scintillation events comprising:
   scintillation means operative in response to received radiation to produce a light-emitting scintillation;
   a plurality of photodetectors of predetermined light receiving aperture and positioned to receive light emitted from said scintillation means as a result of the scintllation event;
   means for directing light from a scintillation event to a plurality of said photodetectors;
   a spatial filter responsive to a plurality of said photodetectors and operative to localize the position of the scintillation event within said scintillation means to a resolution subtantially smaller than the predetermined aperture of said photodetector.

18. The system of claim 17 further including:
a plurality of amplifiers;
each of said photodetectors applying its output signal to a plurality of said amplifiers according to a weighting scheme;
each of said amplifiers corresponding to an elemental resolution dimension within said scintillation means; and
means for identifying when amplifiers corresponding to adjacent resolution dimensions of said scintillation means have opposite amplitude output signals of a predetermined direction, thereby identifying the most probable locus of photo emission within said scintllation means.

19. The system of claim 17 or 18 wherein said directing means includes:
a light guide between said scintillation means and said photodetectors and operative to provide a disbursal of light emitted from said scintillation means as received by said plurality of photodetectors.

20. The system of claim 18 wherein said spatial filter further includes:
means for identifying a first set of adjacent photodetectors receiving light from a scintillation event correlated with receipt of light from a scintillation event by a second set of adjacent photodetectors;
means for localizing the position of scintillation to a fraction of said first set.

21. The system of claim 20 wherein said identifying means includes means for establishing a threshold level of scintillating particle energy as a required condition for identifying said first set.

22. The system of claim 20 or 21, wherein said identifying means includes means for establishing a requirement on the time of occurrence of a scintillation event as a required condition for identifying said first set.

23. A system for sensing the position of scintillation events caused by radiation from a source, comprising:
scintillation means having at least some portions located at positions at opposite sides of said source, with said source including material giving off radiation in opposite directions, said scintillation means being operative in response to received radiation to produce a light-emitting scintillation;
a plurality of photodetectors of predetermined light receiving aperture to receive light emitted from said scintillation means as a result of a scintillation event;
means for directing light from said scintillation means to a plurality of said photodetectors; and,
a spatial filter responsive to the outputs from a plurality of said photodetectors, at least one of which photodetectors is associated with a portion of said scintillation means opposite another portion of said scintillation means, for localizing the position of the scintillation event within said scintillation means to a resolution substantially smaller than the predetermined aperture of each of said photodetectors.

* * * * *